United States Patent
Boonyaratanakornkit et al.

(10) Patent No.: US 9,909,964 B2
(45) Date of Patent: Mar. 6, 2018

(54) METHOD OF PREPARING QUALITY CONTROL MATERIAL FOR FFPE

(71) Applicant: LIFE TECHNOLOGIES CORPORATION, Carlsbad, CA (US)

(72) Inventors: Jerry Boonyaratanakornkit, Davis, CA (US); Erhard Schoenbrunner, Moraga, CA (US); Mona Shahbazian, Martinez, CA (US)

(73) Assignee: LIFE TECHNOLOGIES CORPORATION, Carlsbad, CA (US)

( * ) Notice: Subject to any disclaimer, the term of this patent is extended or adjusted under 35 U.S.C. 154(b) by 679 days.

(21) Appl. No.: 14/340,313

(22) Filed: Jul. 24, 2014

(65) Prior Publication Data

US 2014/0335533 A1 Nov. 13, 2014

Related U.S. Application Data

(63) Continuation of application No. 13/271,813, filed on Oct. 12, 2011, now abandoned.

(60) Provisional application No. 61/392,389, filed on Oct. 12, 2010.

(51) Int. Cl.
| | |
|---|---|
| *C12Q 1/06* | (2006.01) |
| *G01N 1/36* | (2006.01) |
| *G01N 33/574* | (2006.01) |
| *G01N 1/30* | (2006.01) |
| *G01N 1/06* | (2006.01) |
| *G01N 1/28* | (2006.01) |

(52) U.S. Cl.
CPC ............ *G01N 1/36* (2013.01); *G01N 1/30* (2013.01); *G01N 33/574* (2013.01); *G01N 1/06* (2013.01); *G01N 2001/2893* (2013.01); *G01N 2001/366* (2013.01)

(58) Field of Classification Search
CPC ....................................................... C12Q 1/06
See application file for complete search history.

(56) References Cited

U.S. PATENT DOCUMENTS

2006/0154234 A1 7/2006 Winther et al.
2008/0038771 A1 2/2008 Taylor et al.

FOREIGN PATENT DOCUMENTS

| CN | 1420927 | 5/2003 |
| CN | 201381292 | 1/2010 |
| EP | 1250599 | 11/2009 |
| WO | WO-2003/044213 | 5/2003 |
| WO | WO-2010/007509 | 1/2010 |
| WO | WO-2012/051332 A1 | 4/2012 |

OTHER PUBLICATIONS

ACROMETRIX®, "Innovative Molecular Technologies for Standardized Quality Control", *Association for Molecular Pathology 2009 Annual Meeting Presentation*, Nov. 9, 2009, 42 pages.

(Continued)

*Primary Examiner* — Rosanne Kosson
(74) *Attorney, Agent, or Firm* — Baker & Hostetler LLP (57) ABSTRACT

This specification relates to Formalin-fixed embedded quality control material for use for validation, verification, and to run controls for molecular assays. The quality control material can be used for a variety of tissues and for a variety of molecular assays. The quality control material can be used in commercial labs for validation and limit-of-detection analyses.

6 Claims, 3 Drawing Sheets

| KRAS Mutation | Site Test System | Lab 1 SNaPshot | Lab 2 TrimGen Mutector II | Lab 3 DxS | Lab 4 PyroMark | Lab 5 PyroMark | Lab 6 Asuragen | Lab 7 DxS | Lab 8 LDT/non genotyping | Lab 9 Trimgen |
|---|---|---|---|---|---|---|---|---|---|---|
| G12C | 30% | ND | ND | + | + | + | + | ND | + | + |
| | 20% | + | + | + | + | + | + | ND | ND | + |
| | 30% | + | + | + | + | + | + | + | + | + |
| | 5% | + | + | + | - | + | + | + | + | + |
| | 2% | + | - | - | - | - | + | ND | ND | + |
| | 1% | + | - | - | - | - | - | ND | + | - |
| G13D | 30% | ND | ND | + | + | + | + | ND | + | + |
| | 20% | + | + | + | + | + | + | ND | + | + |
| | 30% | + | + | + | + | + | + | + | + | + |
| | 5% | + | + | - | - | + | + | + | + | + |
| | 2% | + | - | - | - | - | - | ND | + | - |
| | 1% | - | - | - | - | - | + | ND | + | - |
| G12V | 20% | + | + | + | + | + | + | ND | + | + |
| | 10% | + | + | + | + | + | + | + | + | + |
| | 5% | + | + | + | - | + | + | + | + | + |
| | 2% | + | + | + | - | - | + | ND | + | ND |
| | 1% | + | + | + | - | - | + | ND | + | - |

(56) References Cited

OTHER PUBLICATIONS

ACROMETRIX®, "Monitoring of KRAS Testing using AcroMetrix® KRAS FFPE Process Controls", *Association for Molecular Pathology 2009 Annual Meeting Abstract*, Nov. 9, 2009, 1 page, as a hit in a Google search.

ACROMETRIX®, "Monitoring of KRAS Testing using AcroMetrix® KRAS FFPE Process Controls", *Association for Molecular Pathology 2009 Annual Meeting Poster*, Nov. 9, 2009, 1 page.

Beer, David G. et al., "Gene-expression profiles predict survival of patients with lung adenocarcinoma", *Nature*, vol. 8 (8), 2002, 816-824.

Do, H et al., "High Resolution Melting Analysis for Rapid and Sensitive EGFR and KRAS Mutation Detection in Formalin Fixed Paraffin Embedded Biopsies", *BMC Cancer*, vol. 8, No. 142, May 21, 2008, 1-14.

Edler, David et al., "Thymidylate Synthase Expression in Colorectal Cancer: A Prognostic and Predictive Marker of Benefit From Adjuvant Fluorouracil-Based Chemotherapy", *J. Clinical Oncology*, vol. 20 (7), Apr. 1, 2002, 1721-1728.

EP11833357, "Supplementary European Search Report dated Sep. 15, 2014", Sep. 15, 2014, pp. 1-7.

Hamann, S et al., "Quantitative intensity/area, semi-automated controls for multiplex immunofluorescence tissue based assays", *FASEB Journal*, vol. 23 Meeting Abstract Suppl., Apr. 1, 2009, Abstract.

Kumar & Rudbeck(Editors), , "Education Guide: Immunohistochemical Staining Methods Fifth Edition", *Dako Press*, chapters 1-21, 2009, 4,11 and 19.

Labourier, E. et al., "Do Pre-Analytical Parameters Explain KRAS Test Sensitivity Disparities?", *The Journal of Molecular Diagnostics*, vol. 14 (6), Nov. 1, 2012, 631-633.

PCT/US2011/056003, , "International Report on Patentability", dated Apr. 25, 2013, 7 pages.

PCT/US2011/056003, , "International Search Report", dated Jan. 31, 2012, 2 pages.

PCT/US2011/056003, , "Written Opinion", dated Jan. 31, 2012, 5 pages.

Schlaberg, R. et al., "XMRV is present in malignant prostatic epithelium and is associated with prostate cancer, especially high-grade tumors", *Proceedings of the National Academy of Sciences*, vol. 106, 2009, pp. 1-7.

Vassiliki, K. et al., "Targeted KRAS Mutation Assessment on Patient Tumor Histologic Material in Real Time Diagnostics", *Plos One*, vol. 4 (11), Nov. 4, 2009, 1-13.

Wigle, et al., *Cancer Research*, vol. 62 (11), 2002, 3005-3008.

FIGURE 1

| KRAS Mutation | Site Test System | Lab 1 SNaPshot | Lab 2 TrimGen Mutector II | Lab 3 DxS | Lab 4 PyroMark | Lab 5 PyroMark | Lab 6 Asuragen | Lab 7 DxS | Lab 8 LDT/non genotyping | Lab 9 Trimgen |
|---|---|---|---|---|---|---|---|---|---|---|
| G12C | 30% | ND | ND | + | + | + | + | ND | + | + |
| | 20% | + | + | + | + | + | + | ND | ND | + |
| | 30% | + | + | + | + | + | + | + | + | + |
| | 5% | + | + | + | - | - | + | + | + | + |
| | 2% | + | + | - | - | - | - | ND | ND | - |
| | 1% | + | - | - | - | - | - | ND | + | - |
| G13D | 30% | ND | ND | + | + | + | + | ND | + | + |
| | 20% | + | + | + | + | + | + | ND | + | + |
| | 30% | + | + | + | - | - | + | + | + | + |
| | 5% | + | - | - | - | - | + | ND | + | - |
| | 2% | + | - | - | - | - | + | ND | + | - |
| | 1% | + | - | + | - | - | + | ND | + | - |
| G12V | 20% | + | + | + | + | + | + | ND | + | + |
| | 10% | + | + | + | - | + | + | + | + | + |
| | 5% | + | + | + | - | - | + | + | + | + |
| | 2% | + | + | + | - | - | + | ND | + | ND |
| | 1% | + | + | + | - | - | + | ND | + | - |

METHOD OF PREPARING QUALITY CONTROL MATERIAL FOR FFPE

CROSS-REFERENCE TO RELATED APPLICATIONS

This application is a continuation of U.S. application Ser. No. 13/271,813, filed Oct. 12, 2011, and claims priority to U.S. application No. 61/392,389, filed Oct. 12, 2010, which disclosures are herein incorporated by reference in their entirety.

FIELD

This specification relates to Formalin-fixed embedded quality control material for validation, verification, and to use as controls for molecular assays.

BACKGROUND

Routine processing of samples in the clinical setting involves formalin fixation and paraffin embedding. FFPE is a highly efficient method that is currently the standard in pathology suites. Formalin-fixed, paraffin-embedded (FFPE) tissues may be stored indefinitely at room temperature, and nucleic acids (both DNA and RNA) may be recovered from them decades after fixation, making FFPE tissues an important resource for molecular assays. However, better methods for developing FFPE materials that mimic actual patient specimens are needed to monitor the performance of molecular assays from FFPE materials and to develop appropriate quality control materials for these assays.

SUMMARY

This specification relates to Formalin-fixed embedded quality control material for use for validation, verification, and to run controls for molecular assays. The quality control material can be used for a variety of tissues and for a variety of molecular assays. The quality control material can be used in commercial labs for validation or verification, including limit-of-detection analyses, precision analyses, method comparison, and accuracy analyses.

Embodiments described herein provide highly reproducible FFPE methods that provide for detection of one or more markers as described in the examples below. Further, these methods allow for the isolation of the DNA from the FFPE with an defined degree of degradation to the sample that mimics the patient sample used for the molecular assay, thereby making it a true control.

Some aspects are methods for preparing a sample for FFPE, including: obtaining a defined concentration of cellular material; mixing the cellular material with a gelling polymer, creating a gel/cellular material; adding the gel/cellular material to a mold with a defined shape until the gelling polymer solidifies; and slicing the solidified material to a uniform and defined size. In some embodiments, the methods also include formalin fixing the sliced solidified material. In some embodiments, the methods also include embedding the material in paraffin. In some embodiments, the mold is a polypropylene cylinder. In some embodiments, the cellular material includes test cells and background cells. In some embodiments, the test cells and/or background cells are chosen from tissue or organs. In some embodiments, the cellular material comprises a known number of test cells and a known number of background cells in a homogeneous mixture. In some embodiments, the test cells comprise at least one marker that is being tested for and the background cells do not have the marker. In some embodiments, the percentage of test cells to background cells is between 0.0001 and 100%. In some embodiments, the percentage of test cells to background cells is between 1 and 100%. In some embodiments, a defined concentration of test cells is admixed with a defined concentration of background cells admixed with a gelling polymer, and formalin-fixed. In some embodiments, the test cells are positive for a test marker and the background cells are negative for the test marker. The test cells can be tissue culture cells, cancer cells, and/or tissue. In some embodiments, the concentration of test cells to background cells is between about 0.0001 to 100%. In some embodiments, the concentration of test cells to background cells is between about 1 and 100%.

Other aspects include kits for preparing samples for FFPE, including: at least one quality control sample for FFPE, according to an embodiment disclosed herein, the sample comprising a first defined concentration of test cells admixed with background cells, wherein the test cells comprise at least a first marker and the background cells do not comprise the first marker. In some embodiments, the test cells are cancer cells. In some embodiments, the marker is a KRAS mutation. In some embodiments, the test cells are colorectal biopsy material. In some embodiments, the kit also includes a second sample containing a second test cell comprising a second marker. In some embodiments, the kit also includes at least one other sample containing a second marker. In some embodiments, the second marker is a second KRAS mutation. In some embodiments, the kit also contains 8 samples comprising the 8 known KRAS mutations associated with colorectal cancer. In some embodiments, the kit also includes a second sample containing a second defined concentration of the test cell admixed with the background cell. In some embodiments, the defined concentration of test cells to background cells is 0.0001 to 100%.

These and other features of the present teachings will become more apparent from the description herein.

BRIEF DESCRIPTION OF THE DRAWINGS

The skilled artisan will understand that the drawings, described below, are for illustration purposes only. The drawings are not intended to limit the scope of the present teachings in any way.

DETAILED DESCRIPTION

It is to be understood that both the foregoing general description and the following detailed description are exemplary and explanatory only and are not intended to limit the scope of the current teachings. In this application, the use of the singular includes the plural unless specifically stated otherwise. Also, the use of "comprise", "contain", and "include", or modifications of those root words, for example but not limited to, "comprises", "contained", and "including", are not intended to be limiting. Use of "or" means "and/or" unless stated otherwise. The term "and/or" means that the terms before and after can be taken together or separately. For illustration purposes, but not as a limitation, "X and/or Y" can mean "X" or "Y" or "X and Y".

Whenever a range of values is provided herein, the range is meant to include the starting value and the ending value and any value or value range therebetween unless otherwise specifically stated. For example, "from 0.2 to 0.5" means 0.2, 0.3, 0.4, 0.5; ranges therebetween such as 0.2-0.3, 0.3-0.4, 0.2-0.4; increments there between such as 0.25, 0.35, 0.225, 0.335, 0.49; increment ranges there between such as 0.26-0.39; and the like.

The section headings used herein are for organizational purposes only and are not to be construed as limiting the subject matter described in any way. All literature and similar materials cited in this application including, but not limited to, patents, patent applications, articles, books, treatises, and internet web pages, regardless of the format of such literature and similar materials, are expressly incorporated by reference in their entirety for any purpose. In the event that one or more of the incorporated literature and similar materials defines or uses a term in such a way that it contradicts that term's definition in this application, this application controls. While the present teachings are described in conjunction with various embodiments, it is not intended that the present teachings be limited to such embodiments. On the contrary, the present teachings encompass various alternatives, modifications, and equivalents, as will be appreciated by those of skill in the art.

Definitions

The term "FFPE" or "formalin fixed paraffin embedded" refers to a method of treating tissues and/or cells by formalin fixing and paraffin embedding the tissues and/or cells and then slicing embedded material typically with a microtome. There are many methods known in the art for FFPE.

The term "gelling polymer" or "gel" is interchangeable and refers to a colloidal suspension of a solid dispersed in a liquid; a semirigid solid.

The term "homogeneous" refers to a mixture that exhibits uniformity. In the context of the mixture of test cells and background cells, the cells are intermixed in a uniform way such that every portion contains approximately the same number of test cells and/or the same number of background cells as other portions (e.g., slices). The ratio of test cells and background cells can vary.

As used herein, the term "mold" refers to a hollow cavity form or matrix into which a liquid or semi-liquid material is placed to take a desired shape upon cooling or drying.

The term "test cell" as used herein refers to a cell that is being tested to determine whether it contains one or more particular markers. Exemplary test cells include but are not limited to, cancer cells, cells from a patient, cells from a biopsy, hematopoietic cells, tissue culture cells, and cells from a tissue.

As used herein, "background cell" "negative cell" and "negative control" are interchangeable and refer to a cell from the same patient or source that does not contain the marker that is being tested for. In some cases, this will be a wild-type cell of the same type as the test cell.

As used herein, the term "patient" refers to any human or animal that is tested and/or treated for disease.

The term "cylindrical" refers to something having the shape of a cylinder, an object shaped like a tube, an object or shape with straight sides and circular ends of equal size. The cylinder can also be a rectangle, square, triangular cylinder and any such shapes.

The term "solidified" or "hardened" are used interchangeably and, with respect to a gel, refers to the ability of a gel to go from a liquid or semi-liquid state to a solid or semi-solid state. In the case of temperature-solidified gels, a polymer is introduced into a cylindrical tube in a fluid form, then allowed to gel to a solid form by cooling. Gels can also be solidified by adding a cross-linker, by motion, and/or by other methods known to those of skill in the art. When using a gel mixed with a cell, it is of interest to choose a gel that does not require extreme heat to form a liquid since this could be detrimental to the cells.

As used herein, the term "fix" refers to a method of preserving tissue. Methods to preserve tissues or cells can be by irreversibly cross-linking proteins.

As used herein, the phrase "quality control" refers to a system for ensuring the maintenance of proper standards in methods to determine whether the process exhibits nonrandom variation.

As used herein the term "marker" and "test marker" are interchangeable and refer to a cellular component specific to a particular disease, whether prognostic, diagnostic, and/or with reference to treatment. The marker may be a DNA, RNA or protein marker. The marker can be any type of mutation associated with a disease. Markers include but are not limited to, translocations, alleles, SNPs, expression profiles, etc. The markers can be DNA, RNA (mRNA, rRNA, tRNA, mitochondrial RNA), or any type of nucleic acid. The markers can be genes, SNPs, microsatelites, translocations, alleles, mutations (e.g., multiple nucleotide and/or large deletions, additions, or changes), multi-RNA complexes, splice variants, transposons, ribozymes, microRNAs (primary, pre- or mature microRNAs), bacterial genomes, plasmids, viral genomes, and viroids. For example, in some embodiments, DNA is used to identify the presence of a SNP. In some embodiments, RNA is used to identify the expression of a SNP.

Overview

This specification relates to Formalin-fixed embedded quality control (FFPE-QC) material for use in validation, verification, and as controls for molecular assays. The quality control material can be used for a variety of tissues and for a variety of molecular assays. The quality control material can be used in commercial labs for validation and limit-of-detection, accuracy and precision analyses.

Embodiments herein provide highly reproducible FFPE methods that provide for detection of one or more markers as described in the examples below. Further, these methods allow for a quality control FFPE product that includes a test cell containing at least one test marker in a background of negative cells. The methods are highly reproducible within a lot and from lot-to-lot and provide for detection of one or more markers as described in the examples below. The marker can be any marker known in the art and can be used to diagnose disease, prognosticate disease and/or to test disease for drug effectiveness. Further, these methods allow for the isolation of the DNA from the FFPE and with controlled degradation to the sample. The test cells and background cells can be admixed in various amounts to identify the limit-of-detection. In use, different concentrations of test cells to background cells can be provided for identifying performance characteristics of a molecular assay in a laboratory. The methods can be used for any type of tissue that would normally be processed into FFPE material. The method involves accurately quantifying the cell concentration and creating a homogeneous mixture of cells containing the marker (test cells) versus background cells (negative cells). The methods involve mixing the cells with a gelling polymer to create homogeneous paraffin-embedded blocks. The methods have the advantage of creating a sustainable, reproducible, and limitless quality control material for FFPE-based diagnostic assays.

The methods include the steps of obtaining a defined concentration of cellular material; mixing the cellular material with a gelling polymer, creating a gel/cellular material; adding the gel/cellular material to a mold with a defined shape until the gelling polymer solidifies; slicing the solidified material to a uniform and defined size, formalin fixing the sliced solidified material, embedding the material in paraffin, and sectioning the material. The resulting FFPE slice can be referred to as the QC sample.

In some embodiments, each of the steps of the above method of preparing a QC FFPE sample is a distinct step. In some embodiments, they may not be distinct steps. In other embodiments, the methods may not have all of the above steps and/or may have other steps in addition to or instead of those listed above. The steps of preparing a QC FFPE sample may be performed in another order. Subsets of the steps listed above as part of preparing a QC FFPE sample may be used to form their own method.

In one embodiment, formalin fixed paraffin embedded quality control materials were constructed by utilizing these methods and materials. The formalin fixed paraffin embedded quality control materials were homogeneous cell cylinders. In short, a defined concentration of cell material containing the target for the diagnostic assay system was obtained. The defined cell concentration was homogenously mixed with a gelling polymer. A mold was used to create a defined shape when the cell-containing polymer solidified. A slicing apparatus was used to separate the cell-containing polymer, shaped with the mold, into a uniform and defined number of pieces. The pieces were formalin-fixed and embedded into paraffin using clinically defined practices. Lastly, a microtome was used to slice the FFPE blocks into sections of defined thickness that can be placed into vials or onto microscope slides.

Currently, the majority of molecular diagnostic assays target liquid-based specimen types (e.g., EDTA plasma, serum, and whole blood) or swab-based specimens (e.g., nasopharyngeal swab and cervical swab). However, recently with cancer-based molecular marker diagnostics, tissue-based diagnostics from FFPE specimen types are typically used. FFPE specimens typically require five processing steps: 1) deparaffinization, 2) reversal of cross linking, 3) extraction, 4) nucleic acid yield test, and 5) amplification/detection which is in contrast to liquid-based specimen diagnostic which requires two processing steps: 1) extraction and 2) amplification/detection.

The quality control FFPE assay, disclosed herein, was evaluated for detection of a KRAS molecular marker as provided in Examples 1-4 herein. Reproducible detection of the KRAS molecular markers was observed after purification of DNA from the FFPE treated cells in a background of negative cells. Labs performing FFPE-based molecular diagnostic tests use synthetic oligonucleotides, cell lines, or patient specimens as quality control material. However synthetic material and cell lines do not control for specific steps in the process and patient specimens are limited in quantity and inconsistent between sections, reducing the utility of the control material for monitoring trending over an extended period of time. A true FFPE quality control material that is homogenous and consistently produced lot-to-lot ensures that laboratories have access to a full process control that can be used over an indefinite period to monitor assay performance.

In certain embodiments, the cells in the FFPE controls can be wildtype or carry known mutations and thereby serve as controls for those mutations. For instance, there are known mutations within the codons 12 and 13 of the KRAS gene that result in the loss of effectiveness of pharmaceutical therapies. Seven mutations (G12D, G12V, G12C, G12S, G12A, G12R, G13D) comprise 98.5% of known KRAS mutations that are involved in drug effectiveness for colorectal cancer. Cell lines for these mutations were obtained and mixed in defined ratios with a cell line containing wild type KRAS. The cell mixtures were mixed with melted agarose cooled to within 10° C. of the gelling temperature and aliquoted into a polypropylene cylindrical mold. The agarose-cell mixture was allowed to solidify at 2-8° C. The cylinder was removed from the mold and placed on a sterile surface. A slicing apparatus was developed with wires spaced 1 mm to 10 mm apart, in certain embodiments the wires can be spaced 1 mm to 5 mm apart. The slicing apparatus was then placed over the cylinder and pressure applied to slice the cylinder into equidistant parts. Each part was then formalin fixed and embedded according to specified manufacturing procedures (see Example 8 below).

Multiplex molecular assays allow for the detection of multiple test cells. Therefore, further embodiments include the step of pooling samples to be tested prior to using the multiplexed assays described herein. For example, different slices with individual mutations can be placed together in 1 tube (to be processed together). For example and without limitation, 1 slice from the G12V and 1 slice from the G12D mutations could be placed together to make a multiplex control (see Table 6).

Cell Material

The cell material can be obtained from any cell, tissue or organ of an organism. The cell material can include one or more prokaryotic cells and/or one or more eukaryotic cells. The eukaryotic cell can be from any eukaryotic organism including, but not limited to, a protozoa, a fungus, a plant, an animal, a human. The animal and/or human cells can be hematopoietic cells. The animal and/or human cells can be cancer cells and/or infected cells. The cells can be tissue culture cells. The cells can be obtained from a biopsy. In some embodiments, a tissue sample is disrupted into cells to prepare a homogeneous material.

In some embodiments, the cell material is a formalin fixed (or other fixed) sample and/or an FFPE sample of tissue. In this case, because it would be difficult or impossible to disrupt the FFPE tissue into separate cells, the cell material can be used for a positive or negative control.

In some embodiments, the cell material contains only test cells. The test cells can be cells that are positive for one or more particular marker or markers. In some embodiments the cell material contains more than one test cell. For example, if two different markers are diagnostic for a particular disease, two different test cells can be included, one test cell being positive for one marker and the other test cell being positive for the other marker. In some embodiments, the cell material also contains background cells. The background cells can be cells from the same or a related source as the test cells, but are cells that do not contain the one or more markers. In some embodiments, the background cells are wildtype cells and or wildtype for the marker. In some embodiments, the test cells may contain more than one marker for a particular disease or diseases and the background cells do not contain any of those markers.

The cell material can contain both test cells and background cells in known amounts. In some embodiments, the amount of test cells to background cells is from about 0.0001 to about 100%, including 0.001, 0.005, 0.006, 0.008, 0.009, 0.01, 0.02, 0.03, 0.04, 0.05, 0.06, 0.07, 0.08, 0.09, 0.1, 0.2, 0.3, 0.4, 0.5, 0.6, 0.7, 0.8, 0.9, and 1%. In some embodiments, the amount of test cells to background cells is from about 1 to about 100%, including but not limited to, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, and 99%. In some embodiments, the amount of the test cell is less than the amount of the background cell. In certain embodiments, the test cells comprise a single marker. In other embodiments, the test cells contained in the cell material comprise more than one marker. For instance, the cell material can contain a defined percentage of a first marker, a defined percentage of a second marker, and so on, as well as a defined percentage of background cells.

In some embodiments, the mixture of test and background cells is homogeneous. However, alternatively, the mixture can be formed such that the test cells are in the middle and the background cells are on the perimeter. Other combinations can be imagined. However, the ratio of test cells to background cells is maintained in the slice, portion or plug, etc.

In some embodiments a series of samples are prepared from cell material of a specific type of test cell with a specific type of background cell in a variety of ratios to use for establishing performance characteristics of a molecular assay. For example, a series of 11 samples having test cell to background cell ratios of 1%, 10%, 20%, 30%, 40%, 50%, 60%, 70%, 80%, 90%, and 100% could be produced to identify the limit of detection of a marker in the test cells using a specific molecular assay.

Gel

The gel used to create the solidified gel/cellular material can be any colloidal suspension of a solid dispersed in a liquid. The gel used can be any gel that can be mixed with cells without changing the properties of the nucleic acid to such an extent that they cannot be assayed. In some embodiments, the gel does not change the properties of the proteins so that they cannot be assayed. The gel can be any gel that can change from a liquid or semi solid state (to be able to mix it with cells) to a solid or gelled state (to allow it to be sliced). In some embodiments, the gel is an agarose, agar, carageenan, pectin, egg yolk, or any type of polymer. In some embodiments, the gel is a polymer that is able to be solidified or hardened. Solidified or hardened refers to the ability of a gel to go from a liquid or semi-liquid state to a solid or semi-solid state. In the case of temperature-solidified gels, a polymer is introduced into an electrophoresis tube in a fluid form, than allowed to gel to a solid form by cooling within the gel. Gels can also be solidified by adding a cross-linker, by motion, and/or by other methods known to those of skill in the art. When using a gel mixed with a cell, it is of interest to choose a gel that does not require extreme heat to form a liquid since this could be detrimental to the cells. Further, when using a gel mixed with a cell, it is also of interest to choose a gel that does not contain inhibitory substance that will inhibit the fixation, embedding, or downstream molecular tests.

Mold

The mold can be any shape known to the skilled artisan that allow for slicing. In some embodiments, the shape of the mold can be a cylinder. The cylinder can be of any length and diameter such that a useful sized slice is produced.

The cylinder can be made of any material that will keep its shape when a hot gel is poured into it. In some embodiments, the material will not stick to the gel/cellular material mixture. In some embodiments, the material will not affect the cellular integrity. In some embodiments, the material can be removed from the solidified gel/cellular material mixture. In some embodiments, the material can be removed without sticking to the gel/cellular material mixture. In some embodiments, the ends of the cylindrical material can be cut off and the tube of hardened gel/cellular material can be slid out. Materials can include polypropylene and equivalent plastic materials. Other materials can be envisioned that might require producing a mold that can be opened and closed, for example glass, metals, and very hard plastics.

Slicing

The cylindrical solidified gel/cellular material can then be sliced into sections of a uniform and defined size. This ensures that the amount of nucleic acid in each slice will be equivalent. The cylindrical solidified gel/cellular material mixture can be sliced using any method known in the art that results in slices of uniform and defined sizes. Any slicer with equidistant slicing ability could be used. In some embodiments, the slicing wires or blades are spaced 1 mm to 5 mm apart. In some embodiments other methods of providing for equivalent samples (e.g., slices) are used. Any tool can be used that provides a sample with a constant volume. Exemplary methods include using a tool to obtain a plug, or using a syringe to obtain an even amount of liquefied sample (e.g., liquefied gel/cellular material).

Fixatives

The cells can be fixed prior to or after formation of the solidified gel/cellular material described above. Chemical fixatives are used to preserve tissue from degradation, and to maintain the structure of the cell and of sub-cellular components such as cell organelles (e.g., nucleus, endoplasmic reticulum, mitochondria). The most common fixative for FFPE is neutral buffered formalin (4-8% formaldehyde in phosphate buffered saline). Fixatives preserve tissues or cells mainly by irreversibly cross-linking proteins. The main action of these aldehyde fixatives is to cross-link amino groups in proteins through the formation of $CH_2$ (methylene) linkage, in the case of formaldehyde, or by a C5H10 cross-links in the case of glutaraldehyde. This process, while preserving the structural integrity of the cells and tissue can damage the biological functionality of proteins, particularly enzymes, and can also denature them to a certain extent. This can be detrimental to certain histological techniques.

In certain embodiments, during the fixation process, glycine (2.5 M) can be added to the suspended cells. The cells are then centrifuged at 1000×g for about 5 to about 20 mins. In certain embodiments, the cells are centrifuged for about 10 mins. After the cells are centrifuged and washed with a buffer, a freezing medium can be added, such as dimethylsulfoxide.

For the methods of preparing QC FFPE controls, the sliced solidified gel/cellular material can be immersed in a fixative, such as a solution with a protein crosslinking activity, such as but not limited to a formaldehyde solution, glutaraldehyde solution, formaldehyde-alcohol mixed solution, alcohol solution, Bouin's solution, Zenker solution, Hely solution, osmic acid solution, Carnoy solution, standard saline citrate (SSC) and RNAeasy™, and equivalents thereof. In some embodiments, the fixative is formalin. In some embodiments, the formaldehyde can be in any kind of buffer. Non-limiting examples of fixative alcohols include thanol and isopropanol. These fixatives are commercially available.

The time of fixation can be from about 2 to 72 hours, including but not limited to 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, and 71 hours. The temperature of fixation can be from about 4° C. to about 26° C., including but not limited to, 5, 6, 7, 8, 9, 10, 11, 12, 13, 14, 15, 16, 17, 18, 19, 20, 21, 22, 23, 24, and 25° C.

Embedding and Sectioning

After the slices have been fixed, they are ready for embedding. During this process the tissue samples are placed into molds along with liquid embedding material (such as agar, gelatin, or wax) which is then hardened. This is achieved by cooling in the case of paraffin wax and heating (curing) in the case of the epoxy resins. The acrylic resins are polymerized by heat, ultraviolet light, or chemical catalysts. The hardened blocks containing the tissue samples are then ready to be sectioned. Because Formalin-fixed, paraffin-embedded (FFPE) tissues may be stored indefinitely at room temperature, and nucleic acids (both DNA and RNA) may be recovered from them decades after fixation, this makes FFPE tissues an important resource for historical studies in medicine. Embedding can also be accomplished using frozen, non-fixed tissue in a water-based medium. Pre-frozen tissues are placed into molds with the liquid embedding material, usually a water-based glycol, OCT, TBS, Cryogel, or resin, which is then frozen to form hardened blocks. The resulting blocks can be sectioned using methods known in the art, including, but not limited to, microtomes, vibratory microtomes and cryostats and the like.

Deparaffinization

Sections can be deparaffinized using methods known in the art and/or commercially available kits. The methods remove the bulk of paraffin from the sample. Various techniques are known for deparaffinizing and include, but are not limited to, washing with an organic solvent or agent to dissolve the paraffin. Solvents include but are not limited to, benzene, toluene, ethylbenzene, xylenes, D-li-monene, octane, and mixtures thereof. These solvents are preferably of high purity, usually greater than 99%. The volume used and the number of washes necessary will depend on the size of the sample and the amount of paraffin to be removed. A sample may be washed between 1 and about 10 times, or between about two and about four times. A typical volume of organic solvent is about 500 ml for a 10 mm tissue sample.

After deparaffinization, samples are preferably rehydrated such as by step-wise washing with aqueous lower alcoholic solutions of decreasing concentrations. Ethanol is a preferred lower alcohol for rehydrations while other alcohols may also be used. Non-limiting examples include methanol, isopropanol, and other C1-C5 alcohols. The sample is alternatively vigorously mixed with alcoholic solutions followed by its removal. In one embodiment, the concentration of alcohol is stepwise lowered.

Uses for FFPE Sections

The sections can be used to isolate DNA or RNA for identification of the presence of a marker and/or for expression of a marker. The markers can be used for diagnosis, prognosis, typing, and/or staging of disease. Markers can include DNA or RNA markers and/or expression levels. Gene expression analyses of various tumor types (breast, lung, prostate and colon) have revealed that there exist numerous subtypes of tumors within each anatomically defined cancer. Furthermore, in some of these studies different subtypes have been linked to a particular prognosis. For example, Wigle et al, (2002 Cancer Research 62 (11) pp. 3005-3008) and Beer et al., (2002 Nature 8 (8) pp. 816-824) demonstrated the existence of particular clusters of genes that are correlated with different disease-free survivals in non-small cell lung cancer. These reports establish that the molecular "make-up" of tumors, as defined by gene expression profiles, has a direct correlation to clinical endpoints such as disease free survival. These retrospective studies strongly suggest that in going forward with prospective trials there is great promise that the molecular make-up of a given tumor will also be directly correlated with whether a patient will respond or not respond to a given therapy. Pharmacogenomic methods can identify patients likely to respond to a particular drug and can lead the way to new therapeutic approaches.

For example, thymidylate synthase (TS) is an integral enzyme in DNA biosynthesis where it catalyzes the reductive methylation of deoxyuridine monophosphate (dUMP) to deoxythymidine monophosphate (dTMP) and provides the only route for de novo synthesis of pyrimidine nucleotides within the cell (Johnston et al., 2002, J. Clinical Oncology, 20(7) pp. 1721-1728). Thymidylate synthase is a target for chemotherapeutic drugs, most commonly the antifolate agent 5-fluorouracil (5-FU). As the most effective single agent for the treatment of colon, head and neck and breast cancers, the primary action of 5-FU is to inhibit TS activity, resulting in depletion of intracellular thymine levels and subsequently leading to cell death.

Other markers that can be tested for include, but are not limited to: HIP1 in the diagnosis and treatment of lymphoma and brain cancers; TS and/or ERCC1 expression levels prognosticate the probable resistance of a patient's tumor to treatment with 5-FU and oxaliplatin-based therapies; recurrent gene fusions of androgen regulated genes and ETS family member genes in prostate cancer; ERBB-1, VEGF, cyclin A, FOS, JUN and MYC in patients with squamous cell lung carcinomas. Additional markers that can be used in accordance with the disclosure include, EGFR, BRAF, PTEN, and PI3K. One of skill will readily note that cells containing any biomarker can be used in accordance with the disclosure and that those disclosed herein represent non-limiting examples.

Hematopoietic cancers or metastases can be tested using the QC FFPE controls. Cancers which involve cells generated during hematopoiesis, a process by which cellular elements of blood, such as lymphocytes, leukocytes, platelets, erythrocytes and natural killer cells are generated are referred to as hematopoietic cancers. Lymphocytes which can be found in blood and lymphatic tissue and are critical for immune response are categorized into two main classes of lymphocytes: B lymphocytes (B cells) and T lymphocytes (T cells), which mediate humoral and cell mediated immunity, respectively. Many of these cancers are characterized by recurrent translocations that can be detected from FFPE using methods discussed herein.

Kits

A "kit," as used herein, refers to a combination of at least one quality control sample for FFPE (e.g., one FFPE slice of the gelled homogeneous mixture of test and background cells). In some embodiments, the kit may contain a combination of quality control samples organized in such a way as to provide controls for all variations of a particular marker. In some embodiments, the variations of the marker are variations of an oncogene that is diagnostic for a particular cancer. In some embodiments the variations of the marker are variations of a mutation in a gene that are prognostic for the usefulness of treating with a drug. In some embodiments, the kit includes a number of different markers that are diagnostic of a particular cancer.

In some embodiments, the marker or markers are for a particular disease. In other embodiments, the marker or markers are for a variety of diseases. In some embodiments, the marker or markers test for drug efficacy for a disease. In some embodiments, the marker or markers test for diagnosis of a disease or a group of related diseases. In some embodiments, the marker or markers test for a series of diseases that have common characteristics and/or symptoms.

The container means of the kits will generally include at least one vial, test tube, flask, bottle, syringe or other packaging means, into which a component can be placed, and in some embodiments, suitably aliquoted. Where more than one component is included in the kit (they can be packaged together), the kit also will generally contain at least one second, third or other additional container into which the additional components can be separately placed. However, various combinations of components can be packaged in a container means. The kits of the present teachings also will typically include reagent containers in close confinement for commercial sale. Such containers can include injection or blow-molded plastic containers into which the desired container means are retained. When the components of the kit are provided in one and/or more liquid solutions, the liquid solution comprises an aqueous solution that can be a sterile aqueous solution.

A kit can also include instructions for employing the kit components as well as the use of any other reagent not included in the kit. Instructions can include variations that can be implemented.

In some embodiments, the kit contains quality control samples for between 1 and 1000 markers and/or test cell to background cell ratios. For example, the kit can contain 11 FFPE quality control slices containing test cells to background cells in concentrations of 1%, 10%, 20%, 30%, 40%, 50%, 60%, 70%, 80%, 90%, and 100%.

Exemplary kits are provided in Examples 6 and 7.

EXAMPLES

Aspects of the present teachings can be further understood in light of the following examples, which should not be construed as limiting the scope of the present teachings in any way. Tables 1-3 provide materials, consumable and instruments used in the following examples. The examples use the KRAS molecular markers to demonstrate the usefulness of the quality control FFPE methods. There are known mutations within the codon 12 and 13 of the KRAS gene that results in the loss of effectiveness of pharmaceutical therapies. 7 mutations (G12D, G12V, G12C, G12S, G12A, G12R, G13D) comprise 98.5% of known KRAS mutations that are involved in identifying the usefulness of chemotherapy on colorectal cancers. Cell lines for these mutations were obtained and mixed and defined ratios with a cell line containing wild type KRAS. The cell mixtures were mixed with melted agarose cooled within 10° C. of the gelling temperature and aliquoted into a polypropylene cylindrical mold. The mold was allowed to solidify at 2-8° C. The cylinder was removed from the mold and placed on a sterile surface. A slicing apparatus was developed by modifying an egg slicer. The slicing apparatus was then placed over the cylinder and pressure applied to slice the cylinder into equidistant parts. Each part was then formalin fixed and embedded according to specified manufacturing procedures (see Example 8 below).

TABLE 1

Materials
Reagents

| Item | Description |
| --- | --- |
| 10% Neutral Buffered Formalin | Formalin used as the fixative reagent in the process. |
| 70% Alcohol | Reagent used in the dehydration process. |
| 95% Alcohol | Reagent used in the dehydration process. |
| 100% Alcohol | Reagent used in the dehydration process. |
| SafeClear | Xylene substitute, used to remove lipids and aid in the transition from dehydration to paraffin. |
| Paraffin | Paraffin used as the embedding medium. |
| 10 mM Tris pH 7.5 | Buffer used to dilute cell mixtures to the appropriate concentration. |
| Low Melting Temperature Agarose | Low melting agarose is used as the copolymer that is mixed with cells and placed into a tube mold. Low melting is used due to the ability of remaining at a liquid state at a lower temperature than standard agarose. The lower temperature reduces the likelihood of lysing cells. |

TABLE 2

Consumables

| Item | Description |
| --- | --- |
| Tissue Molds | Metallic or clear plastic molds used as receptacle for the final stage during paraffin embedding. Mixed agarose cell mixture and liquid paraffin are placed in the mold and allowed to harden. Tissue mold is then removed and discarded. |
| Tissue Cassettes | Agarose cell mixtures after slicing are placed into designated tissue cassettes for fixing and embedding. |
| Tube Mold | A specified mold with a fixed diameter is used as a mold for which the agarose cell mixture is allowed to harden in refrigerated temperatures. Removal of the harden agarose cell mixture is by removing both ends of the mold. |
| Petri Dish | The sterile petri dish allows for a clean environment for which the harden agarose cell mixture is processed. |
| Sterile Forcep | Forceps are used to transfer fixed cell mixtures from the tissue cassettes to the tissue mold. |
| Razor Blade | Sterile razor blade used to remove ends from the agarose cell mixtures. |
| Sterile Disposable Scoops | Scoops used to transfer fragile agarose cell mixtures after slicing into the appropriate reagent filled container. |

TABLE 3

Instruments

| Item | Description |
| --- | --- |
| Microwave | The microwave is used to melt the agarose. |
| Paraffin Embedder | Instrument that contains a reservoir of melted paraffin and cooling block. The instrument is used to dispense paraffin into the tissue mold. The instrument also cools the tissue molds containing the fixed cell mixture and paraffin. |
| Refrigerator | The refrigerator is used to cool the tube mold containing agarose and cell mixtures |
| Incubator/Shaker | The incubator and shaker is used to warm and mix the cell mixtures. The incubator can also be used to melt paraffin. |
| Slicing Apparatus | The slicing apparatus can be a modified egg slicer (base removed). The slicer divides the agarose cell mixture cylinder (after removal from the tube mold) into equivalent mini cylinders. |

TABLE 3-continued

Instruments

| Item | Description |
|---|---|
| Microtome | Microtome is a calibrated instrument used to process FFPE blocks into sections. |

Example 1: Quality Control FFPE Method Using KRAS Markers

Several KRAS point mutations have been shown to correlate with a lack of response to epidermal growth factor receptor (EGFR) inhibitors. As a result, in July of 2009, the FDA updated the "indication and usage" section of the labels of Amgen's Vectibix and ImClone/Bristol-Myers Squibb's Erbitux to note that "retrospective analyses of metastatic colorectal cancer trials have not shown a treatment benefit for the EGFR inhibitors in patients whose tumors had KRAS mutations in codon 12 or 13," and that the use of the drugs is not recommended for the treatment of colorectal cancer patients with these mutations. This label change has led to an increase in KRAS mutation testing.

This example demonstrates the feasibility of manufacturing qualitative formalin-fixed paraffin embedded (FFPE) KRAS Positive Control products. The study demonstrates the ability to manufacture and value assign stock materials from sourced raw materials, the reproducibility of the product, detection of the product on target assays, as well as comparison of the products' DNA quality to those of patient FFPE samples and obtaining a usable DNA yield from a 10 µm section.

The cell lines in Table 4 were obtained from ATCC (Manassas, Va.) and grown to a total of $1.0 \times 10^9$ cells. Stock materials are manufactured in Cell Freezing Media and were value-assigned against the calibrator (quantified by counting with a hemacytometer) using the Roche LIGHT CYCLER™ Control Beta-Globin test.

The cell mixture formulation procedure was performed as follows: 1. values for cell materials stored in the vapor phase of a liquid nitrogen cryogenic freezer were obtained. 2. The stock material was thawed at room temperature. 3. A sterile clean disposable cup was obtained. 4. The appropriate amount of cells containing the target of interest was measured gravimetrically into the sterile cup. 5. The appropriate amount of background cells were measured gravimetrically into the sterile cup (this step is optional). 6. A pre-defined amount of 10 mM Tris pH 7.5 was added into the sterile cup to bring the cells to the appropriate concentration. 7. The sterile cup was placed into a pre-warmed incubator (37° C.) and shaken at 125 RPM for a period of between 20 and 30 minutes.

TABLE 4

Cell lines

| Name | Cell Line |
|---|---|
| KRAS G12A | SW1116 |
| KRAS G12C | SW1463 |
| KRAS G12D | PANC-1 |
| KRAS G12R | PSN-1 |
| KRAS G12S | A549 |
| KRAS G12V | SW480 |
| KRAS G13D | DLD-1 |
| Wildtype | Jurkat cells |

A 1% mixture of Low Melting Temperature agarose was formulated with 10 mM Tris pH 7.5 and microwaved until dissolved. The agarose was placed into a 37° C. incubator and allowed to cool for at least 30 minutes. At this point it was important to not mix the cells until the agarose cooled and equilibrated with the incubator.

The cell mixture and the agarose were mixed as follows: The cell and agarose mixtures were removed from the incubator. They were then aliquoted into a sterile cup by mixing an equal volume of the cell mixture with an equal volume of the agarose mixture. The agarose/cell mixture was placed back into the incubator and shaken at 125 RPM for 10-20 minutes. An appropriately sized tube mold was obtained and labeled. The agarose/cell mixture was poured into the tube mold until the liquid exceeded the upper lip of the tube. The tube mold was capped and the excess liquid was wiped from the mold. If bubbles were present, the tube was reopened and additional liquid (cell/agarose liquid) was added. The tube mold was placed horizontally into a refrigerator at 2-8° C. for a minimum of 1 hour. The tube was inspected to ensure that the agarose had hardened. Both ends of the tube were removed (i.e., the cap was removed from one end and the other end was cut with a scissor). And the agarose cell mixture cylinder was poured into a sterile clean petri dish. The slicing apparatus was cleaned with 70% isopropanol. The Slicing Apparatus was placed over the cylinder to insure the maximum number of equivalent sized mini-cylinders and pressed with equal force through the cylinder until the slicing apparatus reached the bottom of the lid. Using disposable scoops the mini-cylinders were placed into a new sterile cup. If the mini-cylinder was punctured by the scoop during transfer, it was discarded.

The mini-cylinders were formalin-fixed and paraffin-embedded as follows: The sterile cup (containing the mini-cylinders) was filled with 10% neutral buffered formalin. The ratio of formalin to mini-cylinder was at least 10:1. They were incubated at room temperature for 2 hours in the shaker set at 125 RPM (incubation for longer or shorter periods may result in differing DNA fragmentation from lot-to-lot). The fixed mini-cylinders were transferred into labeled tissue cassettes. The tissue cassettes were transferred into a container filled with 70% alcohol and incubated for a minimum of 1 hour. The alcohol was decanted and excess removed using absorbent paper. However, the tissue cassettes were not allowed to dry completely. The tissue cassettes were transferred into a container filled with 95% alcohol and incubated for 1 hour. The alcohol was decanted and excess removed using absorbent paper. However, the tissue cassettes were not allowed to dry completely. The tissue cassettes were transferred into a container filled with 100% alcohol and incubated for 1 hour. The alcohol was decanted and the excess removed using absorbent paper. However, the tissue cassettes were not allowed to dry completely. The tissue cassettes were transferred into a container filled with SAFECLEAR™ and incubated for 30 minutes. The SAFECLEAR™ was decanted and excess removed using absorbent paper. The tissue cassettes were not allowed to dry completely. The tissue cassettes were transferred into a container filled with a 1:1 mixture of Safeclear™ and melted paraffin and incubated for 30 minutes at 65° C. The 1:1 mixture of SAFECLEAR™ and melted paraffin was decanted into a waste container. The tissue cassettes were transferred into container filled with melted paraffin and incubated for 1 hour at 65° C. The melted paraffin was decanted into a waste container. The tissue cassettes were transferred into a container filled with melted paraffin and incubated for 2 hours at 65° C. The fixed mini-cylinders were transferred into a tissue mold containing melted paraffin. The base of the tissue cassette was placed over the tissue mold and paraffin was dispensed from the paraffin embedding instrument until the mold and cassette were filled. The filled tissue mold was placed onto the refrigerated unit of the paraffin embedder and allowed to harden for at least 1 hour. The FFPE blocks were sectioned on a Microtome into the appropriate thickness. The section was transferred using forceps into a sterile tube.

Example 2: Alternate Fixation Process

An alternate fixation process was also performed prior to the formation of the agarose-cell cylinder. In this example, cells as described in Example 1 were pre-fixed with formaldehyde. Cells were suspended in phosphate buffered saline with 5.6% formaldehyde and incubated at 22° C. for 2 hours with shaking 2.5 M glycine was added to a final concentration of 1.8 M and incubated for 5 min at room temperature. Cells were centrifuged at 1000× for 10 min. Supernatant was removed, cells were washed with 5 mL PBS and centrifuged at 1000×g for 10 min. Supernatant was removed and freezing medium (cell culture medium+10% dimethylsulfoxide) was added. The steps of agarose cylinders formation, dehydration and embedding with paraffin then took place as described, for example, Example 1.

Example 3: Reproducibility Analysis

Figure 1:
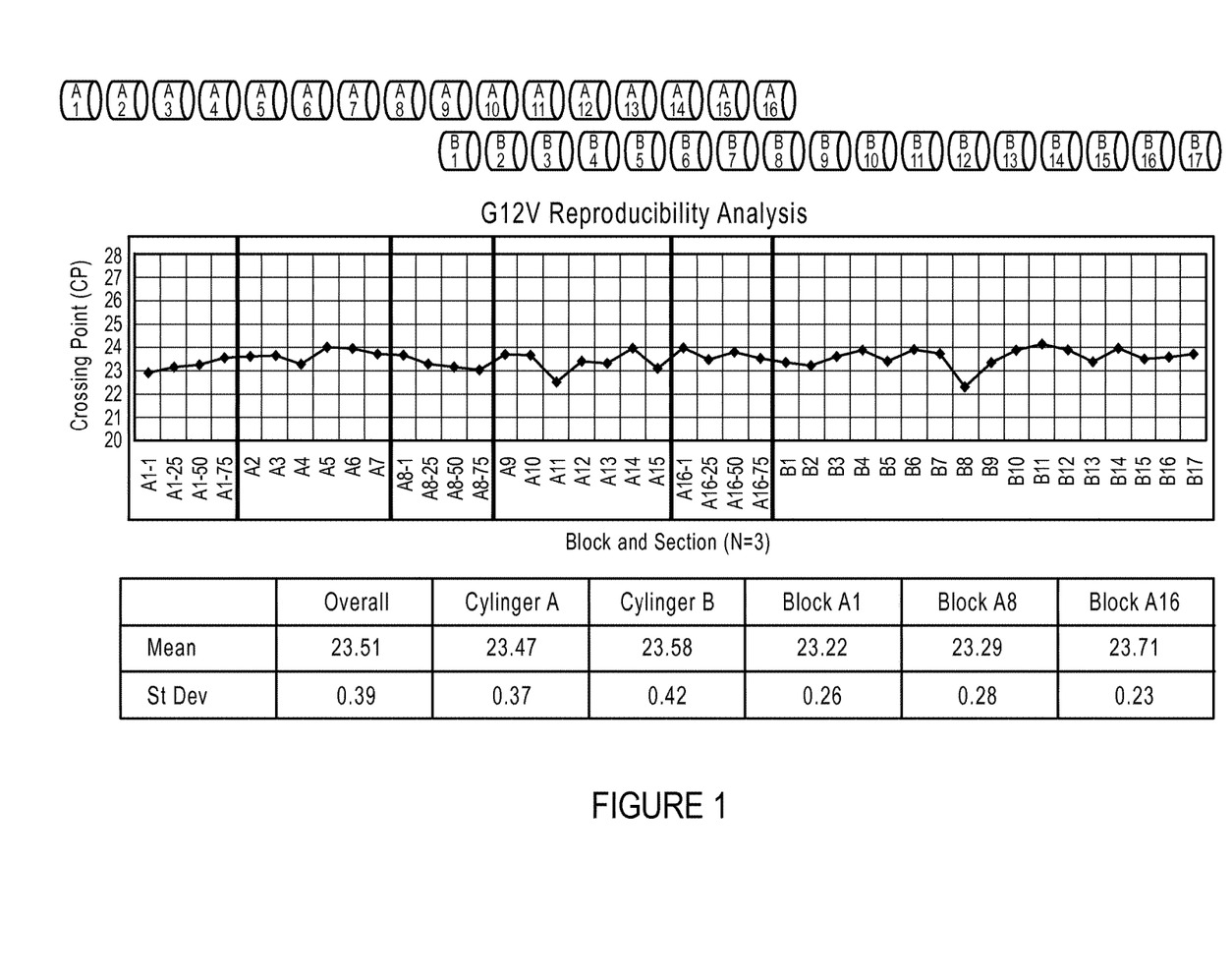
FIG. 1 provides a G12V reproducibility analysis using the FFPE quality control methods.

Two cylinders of KRAS G12V were manufactured using the method of Example 1 and 16-17 blocks were manufactured from each cylinder. Sections were cut from blocks, DNA was extracted, and the DNA was amplified using the Roche LIGHT CYCLER™ Control Beta-Globin test. As shown in FIG. 1, the average crossing points among the blocks for each cylinder were similar, as assessed by low standard deviations. The average crossing points of the blocks between each cylinder were also similar, demonstrating good lot-to-lot reproducibility. The data indicated that the product could be reproducibly manufactured.

Example 4: Detection on Target Assays

Figure 2:
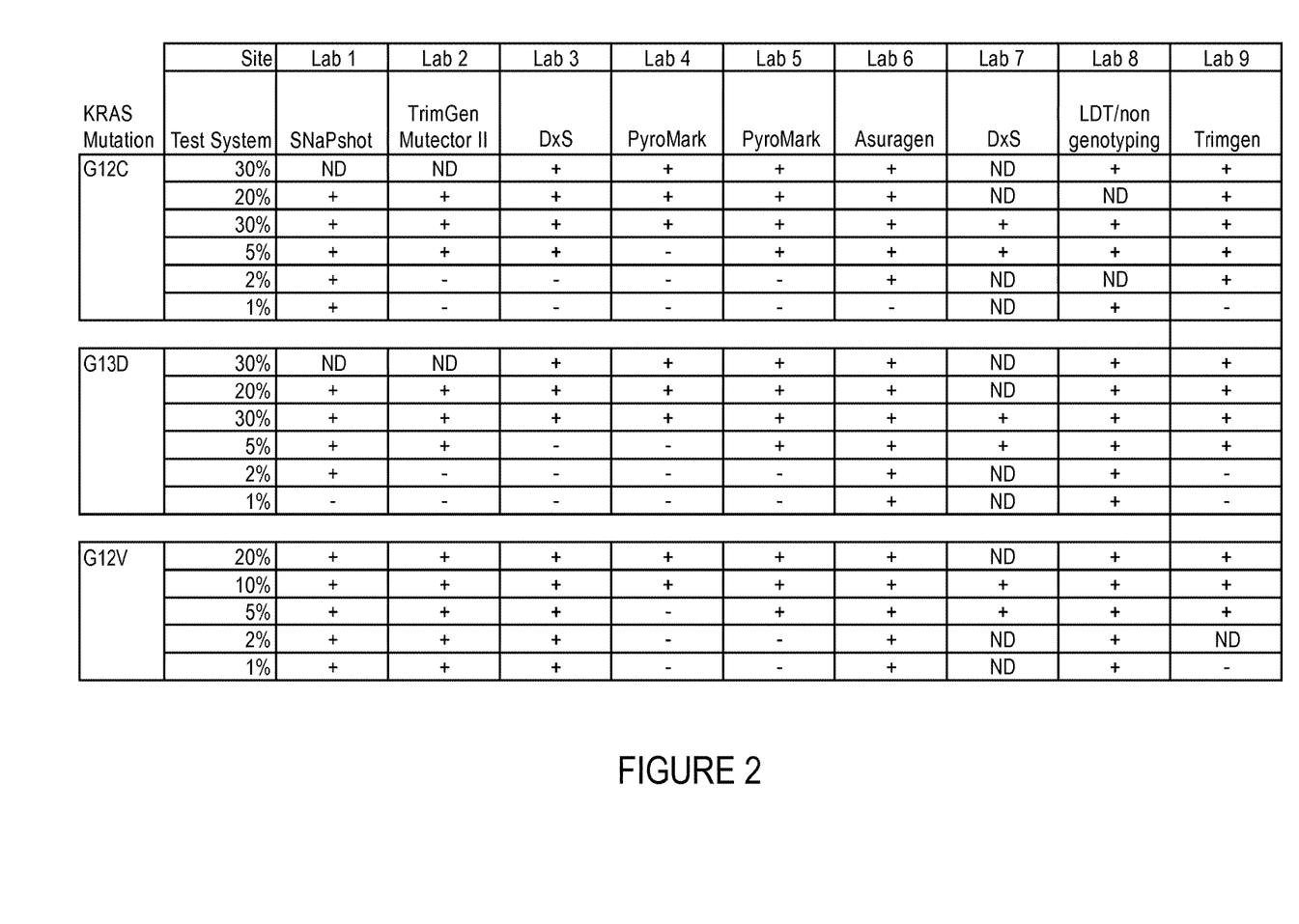
FIG. 2 shows the results from KRAS beta panel testing. A (+) designates that a KRAS mutation was detected using the method, a (−) designates that the KRAS mutation was not detected and an (ND) designates that the test was not run or that it was an invalid run.

A KRAS Beta panel, consisting of 10 μm sections of G12C, G12V, and G13D sections at various percentages (ranging from 1 to 30%) using the method of Example 1 was sent out to a number of laboratories for testing. Results were obtained for various assay platforms including: Life Technologies SNaPshot™, TrimGen™ Mutector II, QIAGEN™/DxS TheraScreen K-RAS, QIAGEN™ PyroMark KRAS, Asuragen Signature KRAS Mutations 7, and a non-genotyping laboratory developed test (LDT). The results are displayed in FIG. 2. A (+) designates that a KRAS mutation was detected using the method, a (−) designates that the KRAS mutation was not detected and an (ND) designates that the test was not run or that it was an invalid run. The results show that the samples worked comparably in all platforms.

Example 5: Analysis of DNA Quality

Figure 3:
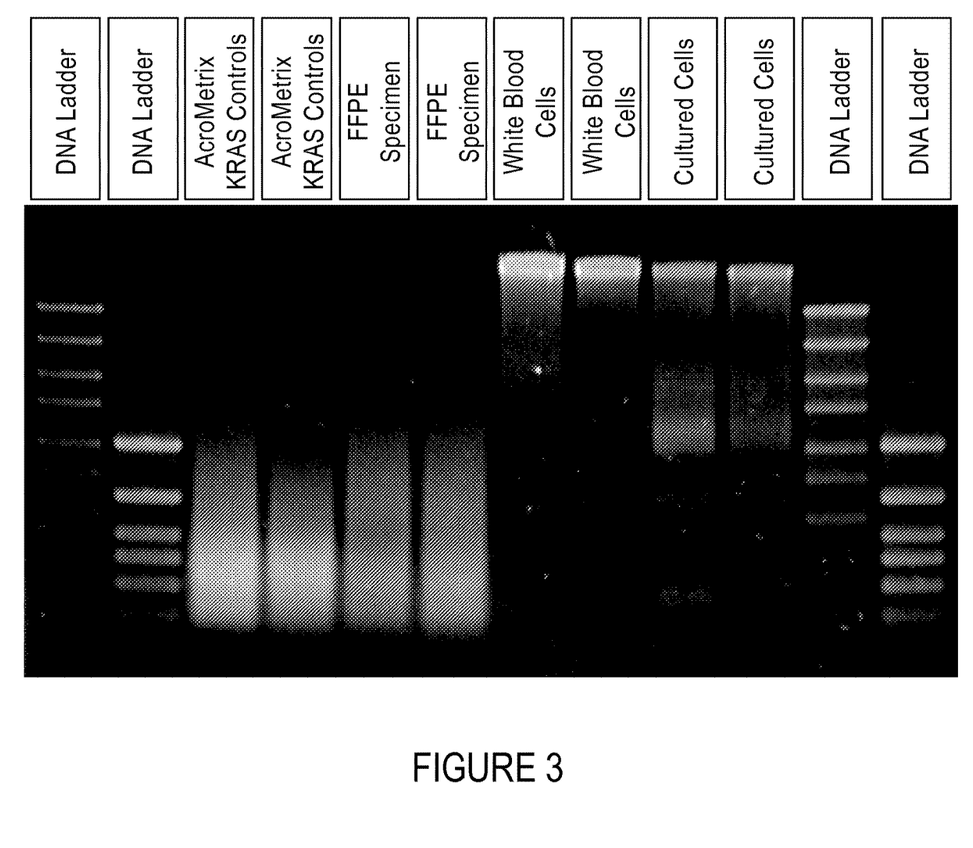
FIG. 3 shows an agarose gel comparing the DNA quality of KRAS DNA isolated from various sources, the sources are in duplicates. The lanes include from left to right: DNA Ladders, AcroMetrix™ KRAS controls, FFPE Specimen, White Blood Cells, Cultured Cells and DNA Ladders.

KRAS DNA was isolated from blood, cultured cells, patient FFPE Tumor, and AcroMetrix KRAS controls (from Example 3). Genomic DNA was isolated using QIAamp® DNA Kits, or the QIAamp® DNA FFPE Tissue Kit. 250 ng of isolated DNA from each sample type were analyzed on a 0.8% agarose gel in duplicates as shown in FIG. 3. Comparing DNA quality, the AcroMetrix KRAS controls were most similar to that of patient FFPE tumor samples showing comparable degradation.

TABLE 5

| | DNA Yield | |
| --- | --- | --- |
| Name | Lot | Average Yield (ng) |
| WT | SL-1 | 679 |
| G12V | SL-1 | 769 |
| WT | SL-2 | 1019 |
| G12V | SL-2 | 683 |
| WT | SL-3 | 728 |
| G12V | SL-3 | 567 |

Genomic DNA was isolated from three lots of KRAS FFPE wildtype and G12V samples (see Example 3) using the QIAamp® DNA FFPE Extraction protocol. Three 10 μm sections were obtained from each sample and extracted to obtain an eluate volume of 50 μL. The DNA yield from each eluate was obtained using the Agilent 8453 UV-visible Spectroscopy System. The average DNA yield from all samples was greater than 200 ng, showing that a usable amount of DNA can be obtained from the AMX KRAS FFPE products.

Example 6: Kit for Analysis of KRAS FFPE Assay Quality Control

There are known mutations within the codon 12 and 13 of the KRAS gene that results in the loss of effectiveness of pharmaceutical therapies. 7 mutations (G12D, G12V, G12C, G12S, G12A, G12R, G13D) comprise 98.5% of known KRAS mutations that have an impact. Cell lines for these mutations were obtained and mixed in defined ratios with a cell line containing wild type KRAS (see Table 4).

A KRAS FFPE kit is prepared containing controls intended for use in assessing the performance of nucleic acid test procedures for the determination of KRAS mutations. See Table 6, 1 vial per KRAS mutation and 1 wildtype (negative control). Routine use of the KRAS FFPE controls enables laboratories to monitor day-to-day assay variation, lot-to-lot performance of assay reagents, and operator variation. The KRAS FFPE controls can also assist in identifying increases in random or systematic error in testing systems.

The KRAS FFPE Controls kit contains controls for 7 major KRAS mutations and a wild type. Each individual control consists of KRAS mutation-positive cells in a synthetic tissue that has been formalin-fixed and paraffin-embedded and sectioned to 10 microns thick.

The KRAS FFPE Controls were designed to meet the need for controls for molecular testing of KRAS in FFPE samples. The independent set of external controls helps to ensure that KRAS nucleic acid testing procedures are consistent across manufacturers, testing laboratories, operators, platforms and assay formats.

The KRAS FFPE Controls are formulated to mimic formalin fixed paraffin embedded tissues and designed to monitor all procedural steps in extracting human DNA from FFPE. The intact human cells allow for the verification of effective DNA extraction and purification. KRAS test methodology includes an extraction step that releases the DNA for amplification and detection, as appropriate to the test.

TABLE 6

KRAS FFPE control kit

| Control name | Quantity |
|---|---|
| KRAS G12A | 1 section per vial >200 ng DNA |
| KRAS G12C | 1 section per vial >200 ng DNA |
| KRAS G12D | 1 section per vial >200 ng DNA |
| KRAS G12R | 1 section per vial >200 ng DNA |
| KRAS G12S | 1 section per vial >200 ng DNA |
| KRAS G12V | 1 section per vial >200 ng DNA |
| KRAS G13D | 1 section per vial >200 ng DNA |
| Wild Type | 1 section per vial >200 ng DNA |

Example 7: Kit for Analysis of EGF-R FFPE Assay Quality Control

An EGF-R FFPE kit is prepared containing controls intended for use in assessing the performance of nucleic acid test procedures for the determination of EGF-R mutations. Routine use of the EGF-R FFPE controls enables laboratories to monitor day-to-day assay variation, lot-to-lot performance of assay reagents, and operator variation. The EGF-R FFPE controls also assist in identifying increases in random or systematic error in testing systems.

The EGF-R FFPE Controls kit contains controls for 29 major EGF-R mutations that are associated with drug resistance to chemotherapy drugs and a wild type (see Table 7 for mutations). Each individual control consists of EGF-R mutation-positive cells in a synthetic tissue that has been formalin-fixed and paraffin-embedded and sectioned to 10 microns thick.

The EGF-R FFPE Control meet the need for controls for molecular testing of EGF-R in FFPE samples. The kit contains 29 slices containing mixtures of EGF-R mutations in a background of wildtype and 1 slice containing only wildtype. The independent set of external controls helps to ensure that EGF-R nucleic acid testing procedures are consistent across manufacturers, testing laboratories, operators, platforms and assay formats.

The EGF-R FFPE Controls are formulated to mimic formalin fixed paraffin embedded tissues and are designed to monitor all procedural steps in extracting human DNA from FFPE. The intact human cells allow for the verification of effective DNA extraction and purification. EGF-R test methodology includes an extraction step that releases the DNA for amplification and detection, as appropriate to the test.

TABLE 7 somatic EGF-R mutations

| Mutation | Exon | Base Change | Cosmic ID |
|---|---|---|---|
| T790M | 20 | 2369C > T | 6240 |
| L858R | 21 | 2573T > G | 6224 |
| L861Q | 21 | 2582T > A | 6213 |
| S768I | 20 | 2303G > T | 6241 |
| G719A | 18 | 2156G > C | 6239 |
| G719S | 18 | 2155G > A | 6252 |
| G719C | 18 | 2155G > T | 6253 |
| Insertions | 20 | 2307_2308ins9 | 12376 |
|  |  | 2319_2320insCAC | 12377 |
|  |  | 2310_2311insGGT | 12378 |
| Deletions | 19 | 2235_2249del15 | 6223 |
|  |  | 2235_2252 > AAT (complex) | 13551 |
|  |  | 2236_2253del18 | 12728 |
|  |  | 2237_2251del15 | 12678 |
|  |  | 2237_2254del18 | 12367 |
|  |  | 2237_2255 > T (complex) | 12384 |
|  |  | 2236_2250del15 | 6225 |
|  |  | 2238_2255del18 | 6220 |
|  |  | 2238_2248 > GC (complex) | 12422 |
|  |  | 2238_2252 > GCA (complex) | 12419 |
|  |  | 2239_2247del9 | 6218 |
|  |  | 2239_2253del15 | 6254 |
|  |  | 2239_2256del18 | 6255 |
|  |  | 2239_2248TTAAGAGAAG > C (complex) | 12382 |
|  |  | 2239_2258 > CA (complex) | 12387 |
|  |  | 2240_2251del12 | 6210 |
|  |  | 2240_2257del18 | 12370 |
|  |  | 2240_2254del15 | 12369 |
|  |  | 2239_2251 > C (complex) | 12383 |

(Note: the cosmic IDs are taken from the Catalogue of Somatic Mutations in Cancer web site sanger.ac.uk/genetics/CGP/cosmic/).

Example 8: Manufacturing Procedure for Sectioning of FFPE Blocks

This manufacturing procedure describes the procedure for the manufacture of FFPE Blocks, as follows:

A sterile cup is filled to the 80 ml line with 10% Neutral Buffered Formalin and swirled until all mini-cylinders (the slices) have separated. The mini-cylinders are placed in 10% Neutral Buffered Formalin for 2 hours at room temperature in the shaker set at 125 RPM, labeled and lidded. The 10% Neutral Buffered Formalin is decanted into the appropriate waste container and the mini-cylinders poured into a sterile Petri dish base. The tissue cassette is placed onto the sterile lid of the Petri dish and mini-cylinders transferred into tissue cassettes. A maximum of the same four mini-cylinders could be placed into one tissue cassette. The lid is closed and tissue cassettes placed into an appropriate container with 70% Alcohol. The volume of the 70% Alcohol reached above the tissue cassettes. A minimum fill at the 80 ml line of the disposable sterile cup is required. It is incubated for a minimum of 1 hour with a maximum of 24 hours. For a hold time of 1 hour, it is incubated at room temperature. Any hold times that exceeded one hour would be incubated at 2-8° C. 70% Alcohol is decanted into a dedicated waste container. The Container is inverted and tissue cassettes are poured over an absorbent paper. The tissue cassettes are transferred into an appropriately-sized container with 95% Ethanol (ensure that the volume of the 95% Ethanol reaches above the tissue cassette). A minimum of approximately 80 mL of 95% Ethanol is required. It is incubated for 55 to 65 minutes at room temperature. The Paraffin Embedder Instrument is turned on. An appropriate amount of paraffin is in each reservoir. The incubator/shaker is turned on and temperature set at 65° C. Clean sterile Polypropylene containers are filled with Paraffin until it reaches the top opening and placed in an incubator shaking at 125 RPM. 95% Alcohol was decanted into an appropriate waste container. The container with the tissue cassettes is inverted and tissue cassettes poured over an absorbent paper (without allowing the tissue cassettes to dry). The tissue cassettes are transferred into an appropriately sized container with 100% Ethanol (ensuring that the volume of the 100% Ethanol reaches above the tissue cassette) and incubated between 60 to 80 minutes at Room Temperature. A minimum of approximately 80 mL of 100% Ethanol is required. The 100% Alcohol is decanted into an appropriate waste container. The container with the tissue cassettes is inverted and tissue cassettes poured over an absorbent paper (without allowing the tissue cassettes to dry). The tissue cassettes are transferred into an appropriately sized container with 100% Ethanol (ensuring that the volume of the 100% Ethanol reaches above the tissue cassette) and incubated between 30 to 40 minutes at Room Temperature. The 100% Alcohol is decanted into a sink with running water. The container with the tissue cassettes is inverted and tissue cassettes poured over an absorbent paper (without allowing the tissue cassettes to dry). The tissue cassettes are transferred into an appropriately sized container with SafeClear™ and the volume of the SafeClear™ made to reach above the tissue cassette and incubated between 30 to 40 minutes at room temperature. The SafeClear™ is decanted into a sink with running water. The container with the tissue cassettes is inverted and tissue cassettes poured over an absorbent paper (without allowing the tissue cassettes to dry). The tissue cassettes are placed into an appropriate container with SafeClear™, ensuring that the volume of the SafeClear™ reaches above the tissue cassette. The tissue cassettes are incubated between 30 to 40 minutes at room temperature. The incubator/shaker was set at 65° C., ensuring that the shaker switch is in the OFF position. Equal volumes of melted paraffin were added with SafeClear and placed in a 65° C.±1° C. incubator. The container with the tissue cassettes is inverted and tissue cassettes poured over an absorbent paper (without allowing the tissue cassettes to dry). The tissue cassettes are transferred into an appropriate container with 50:50 Paraffin/SafeClear™, ensuring that the volume of the 50:50 Paraffin/SafeClear™ reaches above the tissue cassette, and incubated between 30 to 40 minutes at 65° C.±1° C. (Ensuring the Shaker switch is in the OFF position). The 50:50 Paraffin/SafeClear™ was decanted into a disposable container. The tissue cassette was transferred into an appropriate container with Paraffin (ensuring that the volume of the Paraffin reaches above the tissue cassette), and incubated between 60 to 80 minutes at 65° C.±1° C. The Shaker switch is in the OFF position. The Paraffin was decanted into a disposable container. The tissue cassette was transferred into an appropriate container with Paraffin (Ensure that the volume of the Paraffin reaches above the tissue cassette), and incubated between 60 to 80 minutes at 65° C.±1° C. (Ensure Shaker switch is in the OFF position). The Paraffin is decanted into a disposable container. The tissue cassette is transferred into an appropriate container with sample reservoir of the Paraffin Embedder (ensuring that the volume of the Paraffin reaches above the tissue cassettes) and incubated between 120 to 140 minutes.

Paraffin embedding is performed as follows: After incubation the first tissue cassette is removed and placed on a paraffin embedder. Tissue molds are placed into the warmed tissue mold holder. Mini-cylinders are inspected to ensure that they are intact and have significantly shrunk in size. The tissue mold is removed from the tissue mold warmer and paraffin dispensed from a nozzle to fill the bottom of the well. The tissue mold containing paraffin is placed over the cold portion of the paraffin embedder. In a timely manner, a mini-cylinder is placed onto the center of the tissue mold and allowed to cool partially, but not until solid. The tissue cassette is placed without the lid over the tissue mold with the flat surface facing the tissue. The tissue cassette is placed downward (ensure that no air bubbles are trapped within the sample). If air bubbles are present, the tissue cassette is lifted and placed back down until all the air bubbles are removed (ensure that the mini-cylinder is still within the center of the tissue mold). Paraffin is dispensed from the nozzle until the entire bottom of the tissue cassette is covered. Material is carefully transferred and placed on the cold side of the paraffin embedder. This is repeated until all of the mini-cylinders are embedded in paraffin. The embedded cylinders are allowed to cool for a minimum of 30 minutes up to a maximum of 24 hours on the cold side of the embedder. If the material is going to be filled within the next 24 hours, the bulk material is stored at 2-8° C. until filled. If the material is not going to be filled within the next 24 hours, the bulk material is stored at the appropriate storage temperature.

Each embodiment disclosed herein may be used or otherwise combined with any of the other embodiments disclosed. Any element of any embodiment may be used in any embodiment. Although the invention has been described with reference to specific embodiments, it will be understood by those skilled in the art that various changes may be made and equivalents may be substituted for elements thereof without departing from the true spirit and scope of the invention. In addition, modification may be made without departing from the essential teachings of the invention.

What is claimed is:

1. A method for preparing a sample for formalin fixation and paraffin embedding (FFPE), comprising:
    (a) obtaining a defined amount of cellular material comprising a known amount of test cells and a known amount of background cells in a mixture, where the test cells include at least one pre-determined detectable genetic mutation and the background cells do not include the at least one pre-determined detectable genetic mutation;
    (b) mixing the cellular material with a gelling polymer, creating a gel/cellular material;
    (c) adding the gel/cellular material to a mold with a defined shape until the gelling polymer solidifies; and
    (d) slicing the solidified material to a uniform and defined size,
where the ratio of test cells to background cell is maintained in the slice.

2. The method of claim 1, further comprising formalin fixing the cellular material before or after creating a gel/cellular material.

3. The method of claim 1, further comprising embedding the material in paraffin.

4. The method of claim 1, wherein the percentage of test cells to background cells is between 0.0001 and 100%.

5. The method of claim 4, wherein the percentage of test cells to background cells is between 1 and 100%.

6. The method of claim 1 where the amount of test cells is less than the amount of background cells.

* * * * *